US012749565B2

(12) United States Patent
Avila

(10) Patent No.: US 12,749,565 B2
(45) Date of Patent: Sep. 29, 2026

(54) SYSTEM AND METHOD FOR OBTAINING QUALITY IMAGE DATA AND MEASUREMENTS FROM A MEDICAL IMAGING DEVICE

(71) Applicant: Ricardo Avila, Clifton Park, NY (US)

(72) Inventor: Ricardo Avila, Clifton Park, NY (US)

( * ) Notice: Subject to any disclaimer, the term of this patent is extended or adjusted under 35 U.S.C. 154(b) by 283 days.

(21) Appl. No.: 18/375,610

(22) Filed: Oct. 2, 2023

(65) Prior Publication Data

US 2024/0120072 A1 Apr. 11, 2024

Related U.S. Application Data

(60) Provisional application No. 63/413,432, filed on Oct. 5, 2022.

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01)

(58) Field of Classification Search
None
See application file for complete search history.

(56) References Cited

U.S. PATENT DOCUMENTS

2018/0096477 A1* 4/2018 Avila ..................... A61B 6/583
2019/0354882 A1* 11/2019 Sharma .................. G06N 20/00

* cited by examiner

*Primary Examiner* — Lennin R Rodriguezgonzalez
(74) *Attorney, Agent, or Firm* — FALATI

(57) ABSTRACT

The present invention discloses a system and method for obtaining quality image data and measurements from a medical imaging device. The system comprises a medical scanner configured to obtain image of a patient. The system further comprises an artificial intelligence (AI) targeting and image optimization system configured to receive and analyze the image with any combination of model-based methods and AI methods to find one or more target areas of abnormalities. The AI targeting and image optimization system is configured to analyze one or more target areas of abnormality of the image to determine a set of targeted scan parameters for the medical scanner for visualizing and automatically quantitatively measuring the abnormality. The AI targeting and image optimization system is configured to provide information including a target image acquisition parameters to a user to perform an additional targeted image acquisition or image reconstruction.

17 Claims, 4 Drawing Sheets

SYSTEM AND METHOD FOR OBTAINING QUALITY IMAGE DATA AND MEASUREMENTS FROM A MEDICAL IMAGING DEVICE

BACKGROUND OF THE INVENTION

Accurate measurement of abnormalities in medical images is critical for the successful management of numerous diseases and conditions. This is particularly true when measuring the size and other properties of small lung nodules found in computed tomography (CT) scans of the thorax to determine if a nodule is malignant. The current standard of care with currently available CT scanners has good bias and precision performance for volume and linear dimension measurements when the nodule or pathology is large (>1 cm diameter). However, with decreasing nodule size the bias and precision performance of size measurement systems (scanner, acquisition protocol, measurement algorithm) degrades significantly. In addition, the number of lung nodules present in the lungs increases as the size of the nodule decreases, creating large numbers of small lung nodules that are difficult to measure and characterize. These two factors make accurate malignancy assessment of small lung nodules important and highly challenging for large numbers of patients and physicians.

The technical performance of CT scanners has improved substantially over the last twenty years. Most CT scanners are now capable of generating numerous thin CT slices of patient anatomy with slice thickness and slice spacing of less than 1 mm. However, most radiologists are unwilling to scan patients with the highest resolution acquisition parameters because this results in many more CT images. The more CT images generated by a CT scanner, the longer it takes for a radiologist to review a CT scan and report on findings. It is thus common for a single CT scan to be acquired of a patient's lungs and the acquisition parameters (e.g. slice thickness and spacing) are not the best that a CT scanner can achieve, even given a low radiation dose requirement. In addition, the set of acquired CT images is then used for both detection and quantitative measurement of abnormalities (e.g. size and size change).

Along with the numerous technical advancements that have been made to modern day CT scanners there has also been a large increase in scanner complexity. Most CT scanners now have over a dozen different acquisition parameters specifying numerous new capabilities including, but not limited to, new variants of reconstruction kernels (e.g., iterative recon), new filters (e.g., tin), auto tube current and power modulation methods, and new multi energy image acquisition capabilities. Many of these acquisition features are complex and it is very difficult to predict in advance the impact of these many acquisition parameters on the resulting CT image quality and pathology measurement performance. This complexity is yet another factor that encourages healthcare institutions to establish a single CT image acquisition protocol for a clinical application and use the resulting CT images for all downstream care tasks. Further complicating matters, the quality of a CT image differs depending on location in the CT scanner geometry (e.g. distance from iso-center) and due to patient abnormality presentation and surrounding anatomy (e.g., bone can cause beam hardening).

Artificial Intelligence (AI) systems (deep learning and more traditional model-based methods, for example McCulloch Acad Radiol. 2004) have improved over the last two decades and can provide high performance detection of abnormalities including CT lung nodules. In addition, model-based segmentation and measurement algorithms have been developed that have the ability to adapt to the fundamental characteristics of an acquired image such as 3D resolution, sampling rate and noise. This fundamental image calibration information has also been shown to be useful when used by a simulation algorithm to predict bias and precision volume measurement performance for small lung nodules.

Current standard clinical practice is that CT images of abnormalities are not acquired at the best acquisition settings for a quantitative measurement or analysis of a single abnormality, but instead, are acquired at settings that are generally optimized for radiologist subjective viewing.

Therefore, there is a need for a system and method for significantly improving the quality of acquired image data of medical imaging devices to improve detection and quantitative measurements of target objects including but not limited to detection and measurement of health conditions and diseases.

SUMMARY OF THE INVENTION

The present invention discloses a system and method for obtaining quality image data and measurements from a medical imaging device. The system comprises a medical scanner configured to obtain image of a patient. The system further comprises an artificial intelligence (AI) targeting and image optimization system configured to receive and analyze the image with any combination of model-based and deep learning AI methods to find one or more target areas of abnormalities. The AI targeting and image optimization system is configured to analyze one or more target areas of abnormality of the image to determine a set of targeted scan parameters for the medical scanner for visualizing and automatically quantitatively measuring the abnormality. The AI targeting and image optimization system is configured to provide information including a target image acquisition data to a user to perform an additional targeted image acquisition or image reconstruction.

In one embodiment, the medical scanner is monitored and optimized using an automated calibration phantom monitoring and optimization system. In another embodiment, the AI targeting and image optimization system is configured to calculate automated measurement of the abnormality with the target image acquisition data.

In one embodiment, the medical scanner is at least one of Computed Tomography (CT), Magnetic Resonance (MR), Positron Emission Tomography (PET), X-ray Radiography (XR), and Ultrasound (US) scanner.

In one embodiment, the generated target image acquisition data includes the set of targeted scan parameters. The targeted scan parameters are determined by any combination of a calibration optimized protocol database, model-based analysis methods, deep learning AI analysis methods, simulation methods, and prior clinical guidance information.

In another embodiment, the generated target image acquisition data includes a set of targeted scan parameters, a recommended automated measurement algorithm, and optimized analysis algorithm parameters. The targeted scan parameters and automated measurement algorithms are determined by any combination of a calibration optimized protocol database, model-based analysis methods, deep learning AI analysis methods, simulation methods, and prior clinical guidance information.

In one embodiment, the automated measurement algorithm uses an image formation simulation engine to estimate automated measurement properties including predicted measurement bias and measurement precision. In another embodiment, the analysis of the target areas for assessing the severity of the abnormality is performed based on fundamental image quality characteristics of the image. In one embodiment the image quality characteristics includes resolution, noise and sampling rate. In another embodiment the AI targeting and image optimization system is configured to enable the user to select one or more target areas of abnormality of the image to determine the targeted scan parameters. In one embodiment, the AI targeting and image optimization system is further configured to provide a radiological image viewer to display both the image and targeted images from targeted image acquisition in a same viewing window using registered image overlays.

In one embodiment, a method for obtaining quality image data and measurements from a medical imaging device is disclosed. At one step, a medical scanner configured to obtain image of a patient. At another step, an artificial intelligence (AI) targeting and image optimization system is configured to receive and analyze the image with any combination of model-based and deep learning AI methods to find one or more target areas of abnormalities. At yet another step, the AI targeting and image optimization system is configured to analyze one or more target areas of abnormality of the image to determine a set of targeted scan parameters for the medical scanner for visualizing and automatically quantitatively measuring the abnormality. At yet another step, the AI targeting and image optimization system is configured to provide information including a target image acquisition parameter data to a user to perform an additional targeted image acquisition or image reconstruction.

At yet another step, the AI targeting and image optimization system is configured to calculate automated measurement of the abnormality with the target image acquisition data. At yet another step, the AI targeting and image optimization system is configured to provide a radiological image viewer to display both the image and targeted images from targeted image acquisition in a same viewing window using registered image overlays.

The medical scanner is at least one of Computed Tomography (CT), Magnetic Resonance (MR), Positron Emission Tomography (PET), X-ray Radiography (XR), and Ultrasound (US) scanner.

In one embodiment, the generated target image acquisition data includes the set of targeted scan parameters. The targeted scan parameters are determined by any combination of a calibration optimized protocol database, model-based analysis methods, deep learning AI analysis methods, simulation methods, and prior clinical guidance information.

In another embodiment, the generated target image acquisition data includes a set of targeted scan parameters and automated measurement algorithms. The targeted scan parameters and automated measurement algorithms are determined by any combination of a calibration optimized protocol database, model-based analysis methods, AI analysis methods, simulation methods, and prior clinical guidance information.

In another embodiment, the automated measurement algorithm uses an image formation simulation engine to estimate automated measurement properties including measurement bias and measurement precision. The analysis of the target areas for assessing the severity of the abnormality is performed based on fundamental image quality characteristics of the image to determine the targeted acquisition settings. The image quality characteristics includes resolution, noise and sampling rate.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Figure 1:
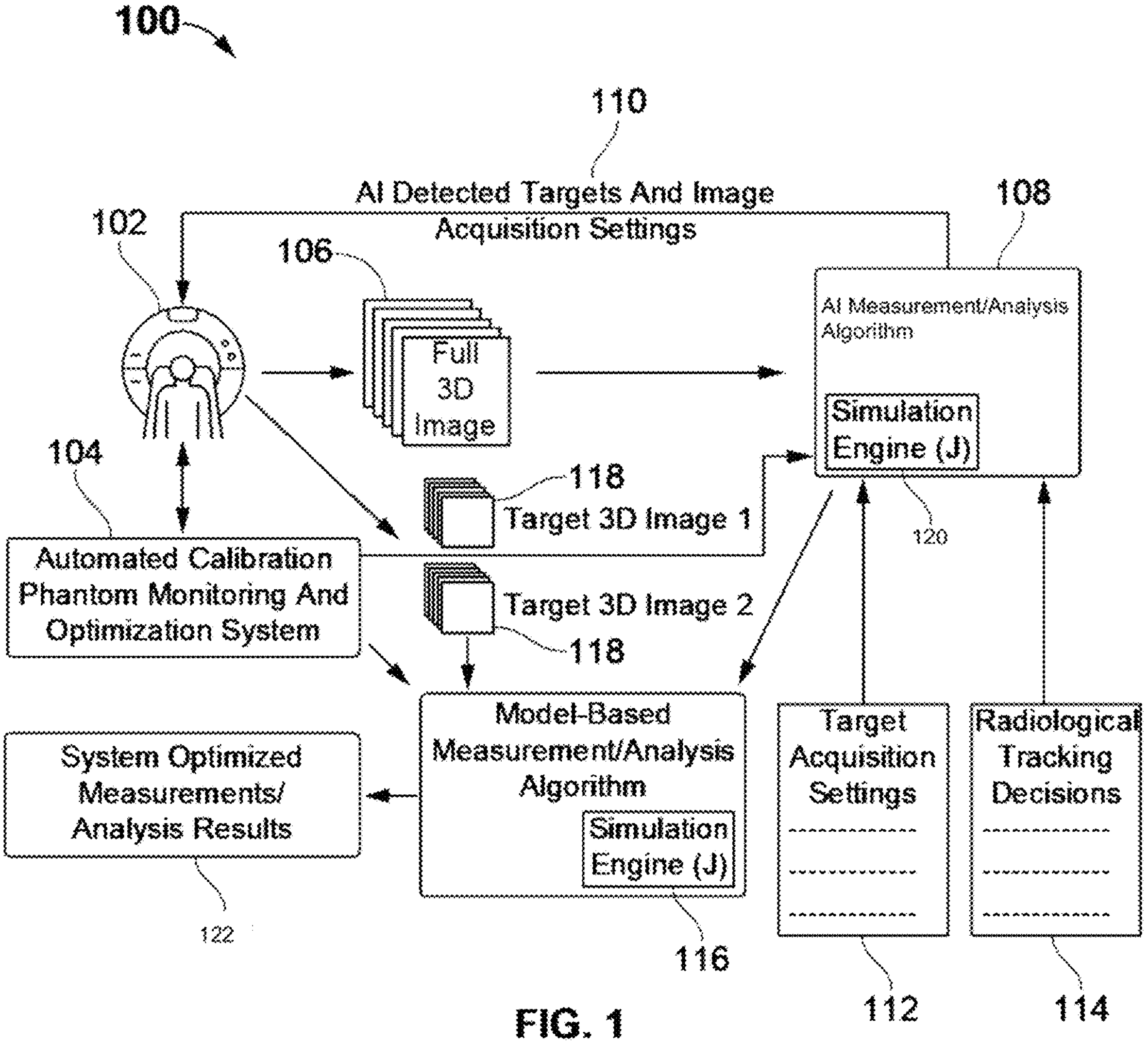
FIG. 1 exemplarily illustrates an environment of a system for obtaining quality image data and measurements from a medical imaging device, according to an embodiment of the present invention.

The present disclosure discloses a system and method for significantly improving the quality of acquired image data of medical imaging devices to improve detection and quantitative measurements of target objects including but not limited to detection and measurement of health conditions and diseases.

A description of embodiments of the present disclosure will now be given with reference to the figures. It is expected that the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

Before any embodiments of the invention are explained in detail, it is to be understood that the disclosure is not limited in its application to the details of construction nor to the arrangement of components set forth in the following description or illustrated in the drawings. The disclosure is capable of other embodiments and of being practiced or of being carried out in various ways.

Referring to FIG. 1, an environment 100 comprises a medical scanner 102 for scanning a patient. The medical scanner 102 is monitored and optimized using an automated calibration phantom monitoring and optimization system 104. When the scanner 102 scans a patient a full 3D image acquisition dataset 106 is rapidly and electronically sent to an AI targeting and image optimization system or AI system 108. The AI targeting and image optimization system 108 then detects pathologies and abnormalities in the original full 3D image 106 and computes targeted scanner data 110 comprising a set of target 3D acquisition protocols, and image processing methods designed to optimize the image data for the quantitative measurement/analysis clinical tasks needed for each target. The AI system 108 could potentially consult a list of saved target acquisition settings 112 and previous radiological tracking decisions 114 that determine the pathologies/abnormalities that will be considered for a targeted acquisition and steps to obtain the acquisitions. The list of target acquisition settings 112 also include additional properties and requirements of the target acquisitions (e.g., radiation exposure limits), potentially making decisions based on abnormality features/types (e.g., part-solid vs. solid lung nodules).

The AI system 102 also may leverage a simulation engine 116 that could give quantitative performance prediction information of an image acquisition protocol and measurement algorithm. While the patient is still on the table the scanner, the operator decides, with potential consultation with the radiologist, which AI detected targets to either scan again with the high-quality image acquisition settings and methods or to perform an additional reconstruction with already acquired targeted scanner data 110. A set of high-quality target image acquisitions 118 is then acquired and used to perform AI measurement/analysis 120, which may use the simulation engine 116, and the AI detections and high-quality measurement results 122 are then available to the user, for example, radiologist for review along with the acquired images.

The system of the present invention is detailed explained as follows. The system comprises medical scanner 102, the automated calibration phantom monitoring and optimization system 104 and an automated scan targeting and measurement system. In one embodiment, the medical scanner is at least one of Computed Tomography (CT), Magnetic Resonance (MR), Positron Emission Tomography (PET), X-ray Radiography (XR), and Ultrasound (US) scanner. The automated scan targeting and measurement system along with the scanner 102 is configured to 3D scan a patient according to the image viewing preferences of the user, for example, a radiologist. The automated scan targeting and measurement system and the scanner 102 are potentially guided by the automated calibration phantom monitoring and optimization system 104, and then rapidly and automatically send the acquired CT images or image to the AI system 108. The AI system 108 is configured to automatically detect diseases and abnormalities in the three-dimensional scan.

The AI targeting and image optimization system 108 is configured to analyze one or more target areas of abnormality of the image to determine a set of targeted parameters for the medical scanner for visualizing and automatically quantitatively measuring the target abnormality. The AI targeting and image optimization system 108 is configured to provide an information including a target image acquisition settings to an operator to perform an additional targeted image acquisition or image reconstruction. The targeted image acquisition data includes a set of targeted parameters. The AI targeting and image optimization system 108 is configured to provide a targeted CT image acquisition request. The request includes the targeted image acquisition data and best known or calculated image acquisition protocol for the intended clinical measurement and/or analysis task (e.g., nodule volume change measurement). To achieve the highest efficiency, the first scan of the patient should be analyzed by the AI targeting and image optimization system 108 while the patient is on the CT table so another patient visit to acquire high quality target images of the abnormalities is not needed.

The system is configured to enable a user to customize the target areas that need additional high quality image acquisitions or reconstructions, for example, CT image acquisitions or reconstructions. For example, the user could specify that only nodules that fall in a specific size range (5 to 12 mm nodules), with evidence of high disease severity features (e.g., nodule spiculation). Then, the AI targeting and image optimization system 108 will present such additional data collection candidates to the technologist for an additional targeted high-quality acquisition or additional targeted reconstructions.

The AI targeting and image optimization system 108 has the ability to analyze each target pathology (e.g., lung nodule) and could customize the target CT acquisition protocol to produce the highest quality data for model-based measurement and analysis. For example, one nodule may exhibit a large amount of motion or streaking artifacts which can be overcome by acquiring multiple CT image acquisitions and combining the acquisitions, with automated registration to align the separate acquisitions, to minimize the artifacts. This may be needed if artifacts and biases in the images are related to the location of an object within the CT helical pitch geometry/path, which influences the amount and location of artifacts in a CT image. In one embodiment, the system could work with the CT scanner to make sure that multiple acquisitions are performed such that the target location is positioned at different locations in the helical pitch (or even using different helical pitch settings per acquisition).

In addition, if the originally detected nodule is in an area of high noise, the targeted scan could be performed with higher radiation dose, or dual energy settings to help reduce noise of the high-quality target image acquisition. To arrive at the optimal target image acquisition the AI targeting and image optimization system 108 is provided with the clinical tasks being performed for the imaging study. One task may be to detect and quantitatively measure suspicious lung nodules while another task may be to detect and measure areas of emphysema and another may be to measure bronchial wall thickness. The target image acquisition settings and required fundamental target image quality properties (resolution, sampling, noise, linearity, spatial warping) for these three different tasks may differ in order to achieve the highest measurement/analysis algorithm performance.

The selection of the best target acquisition could be improved by using the simulation engine 116 and a model of the scanner and the nodule being targeted. For example, the simulation engine 116 could generate thousands of simulated images of a target nodule (estimated from the original 3D full scan) for a proposed acquisition protocol and measure them with a deep learning AI or model-based measurement algorithm, which could be used to produce a set of volume measurements with an expected bias and precision. If this is done for numerous candidate target acquisition protocols the simulation results (bias and precision), several different methods could be compared to help select the best target acquisition protocol.

Routine acquisition and analysis of CT image 3D calibration phantom scans, including from a table phantom that rests below a patient during scanning, results in the estimation of fundamental image quality properties such as 3D resolution, 3D sampling rate, CT linearity, image noise and spatial warping at different distances from the scanner iso-center (e.g. out to 160 mm). This automated phantom analysis information is then useful for optimizing deep learning AI or model-based algorithms to detect objects, including edge boundaries of lesions, the location of vessels, and correcting for biases. This calibration information could also be used with the simulation engine 116 to produce estimates of measurement precision and bias, and performing measurement bias correction.

Further, one of the important considerations when specifying a high-quality image acquisition of a suspected target abnormality is the resolution and sampling rate of the high-quality target acquisition. Fully automated image calibration phantoms are used routinely to automatically estimate the resolution of a CT scan at different distances from the scanner iso-center, allowing clinical sites to quickly establish and verify the 3D resolution of the best image acquisition protocol (including reconstruction kernel, collimation, slice thickness, and other parameters) available for a specific CT scanner. Once the distance of the abnormality from scanner iso-center has been calculated, the optimal 3D sampling rate (e.g., Nyquist criteria), given the radiation dose limits and scanner resolution, could be calculated based on the fundamental physics tradeoffs between resolution, noise and radiation dose. In addition, the maximum amount of noise that is needed for a high-quality AI deep learning or model-based measurement/analysis must be factored in to arrive at the optimal targeted image acquisition. In general, a target acquisition, which could be the entire patient width, should be optimized for a clinical task, or set of tasks, and should attempt to adhere to basic principles in medical physics (e.g., image noise vs. resolution given a constant radiation dose level) and signal processing such as the Nyquist criteria and others.

A potential feature of this system is for the AI abnormality detection system to retain a per patient memory of abnormalities being tracked (or explicitly not tracked) so that future recommended targeted acquisitions are only performed in line with previous radiological requests. This would avoid having a system acquire unnecessary data at a later study time point. For example, a radiologist could explicitly ask the system to track and target an abnormality over time or explicitly not track a specific abnormality that has been determined not to be a concern.

The system could potentially take a high-quality target scan, and after further analysis of the newly acquired target scan, recommend additional target scans at the same location or at different locations within the patient. In this way the system could detect and analyze patient image or image data while the patient remains on the scanner table. The decision to acquire the next set of images could be guided by deep learning AI, model-based algorithms, physics or math or computer vision theory, and potentially simulation.

The system could also potentially provide the user, for example, a technologist with a set of targets to measure multiple diseases and conditions and all of the information could be transferred electronically to the scanner interface so that the technologist could easily accept or reject a proposed target acquisition. This would save time of the technologist to enter the necessary protocols and would likely yield fewer protocol entry mistakes.

While the examples described have focused on acquiring CT images to address a single disease, the present invention also supports identifying and acquiring high quality images of a set of targets which each may help manage multiple disease. For example, a CT scan acquired to detect early lung cancer may also result in an AI generated set of high-quality acquisitions to measure cardiac, vascular, and COPD abnormalities.

The system is useful for many potential clinical applications using CT. In general, any clinical application that involves very precise and high-quality imaging will benefit from this approach. This could include sizing and assessing the fit of stents and other objects in vascular and other anatomy as well as sizing and planning the placement of prosthetics. Another application could include the analysis of fractures to better visualize bone trauma. There are many more potential clinical applications that need the best imaging available to better manage a patient.

This system and method could also be applied to other imaging modalities and clinical applications such as Magnetic Resonance Imaging (MRI), X-ray Radiography (XR), Ultrasound (US), and Positron Emission Tomography (PET).

The data produced by automated targeting and optimized acquisition could be stored in a format such that the targeted scans are "linked" to the original scan including any math transformation needed to properly position the targeted scan in the original scan. With this combined information new types of radiological viewing applications could be built that could allow the radiologist/user to easily switch back and forth between viewing and measuring the original scan and showing the high-quality targeted scan and measurements embedded in a view of the original scan.

Another potential feature is to provide the technologist with a way to obtain approval from a radiologist to scan the targeted region by having the system send a text or some other communication to the radiologist with information on the high-quality target scanning request.

One aspect of the present disclosure is directed to a method for obtaining quality image data and measurements from a medical imaging device, comprising the steps of: operating a medical scanner to obtain an image of a subject; analyzing the image with any combination of model-based and deep learning AI methods to find one or more target areas of abnormalities; analyzing one or more target areas of abnormality of the image to determine a set of targeted scan parameters for the medical scanner for visualizing and automatically quantitatively measuring the abnormality; and providing information including a target image acquisition data to a user to perform an additional targeted image acquisition or image reconstruction. In one embodiment, the method further comprises calculating automated measurement of the abnormality using the target image acquisition data. In another embodiment, the method further comprises providing a radiological image viewer to display both the image and targeted images from targeted image acquisition in a same viewing window using registered image and measurement overlays.

Another aspect of the present disclosure is directed to a system for obtaining quality image data and measurements from a medical imaging device, comprising: medical scanner configured to obtain image of a patient; and an artificial intelligence (AI) targeting and image optimization system configured to: receive and analyze the image with any combination of models and AI methods to find one or more target areas of abnormalities, analyze one or more target areas of abnormality of the image to determine a set of targeted scan parameters for the medical scanner for visualizing and automatically quantitatively measuring the abnormality, and provide information including a target image acquisition data to a user to perform an additional targeted image acquisition or image reconstruction. In one embodiment, the medical scanner is monitored and optimized using an automated calibration phantom monitoring and optimization system. In one embodiment of the system, the target image acquisition data includes the set of targeted scan parameters, wherein the targeted scan parameters are determined by any combination of a calibration optimized protocol database, model-based analysis methods, deep learning AI analysis methods, simulation methods, and prior clinical guidance information. In another embodiment of the system, the target image acquisition data includes a set of targeted scan parameters and automated measurement algorithms, wherein the targeted scan parameters and automated measurement algorithms are determined by any combination of a calibration optimized protocol database, model-based analysis methods, deep learning AI analysis methods, simulation methods, and prior clinical guidance information.

Another aspect of the present disclosure is directed to a method for obtaining quality image data and measurements from a medical imaging device, comprising the steps of: operating a medical scanner to obtain an image of a subject; analyzing the image with any combination of model-based methods and deep learning AI methods to find one or more target areas of abnormalities; analyzing one or more target areas of abnormality of the image to determine a set of targeted scan parameters for the medical scanner for visualizing and automatically quantitatively measuring the abnormality; providing information including a target image acquisition data to a user to perform an additional targeted image acquisition or image reconstruction, wherein the target image acquisition data includes the set of targeted scan parameters; and calculating automated measurement of the abnormality using the target image acquisition data.

Experimental Results:

An initial experiment is conducted, where 3D printed 6.0×3.6×3.6 mm with 1.25 mm diameter cylinders passing through them were placed in an Accumetra CTLX2 phantom and CT scanned on a GE Lightspeed VCT scanner. Five independent and full 3D scan low dose CT scans of the CTLX2 phantom were performed with standard lung cancer screening acquisition parameters of 1.25 mm slice thickness, 1.25 mm slice spacing, and the STANDARD reconstruction kernel. Five independent targeted scans of the ellipsoid object region (inside the CTLX2) were also obtained with a small Field of View (FOV) and with 0.625 mm slice thickness and 0.2 mm slice spacing and 3 times higher dose than the first lower slice thickness scan.

The volume is measured for the same 6 mm longest diameter ellipsoids quantitatively in each of the five scans using a CT small lung nodule volume measurement algorithm. For the full 3D scans the coefficient of variation (CV) for the volume measurements was 7.90%. Volume measurement of the targeted acquisitions of the same exact objects produced a CV of 2.58%, representing a 3.06 times improvement over the original 3D full scan results. These preliminary results illustrate the potential of the approach to significantly improve quantitative measurements. However, further improvements are possible if the volume measurement algorithm is better optimized to work on targeted acquisitions and work with advanced quantitative algorithms and a simulation engine.

Figure 2:
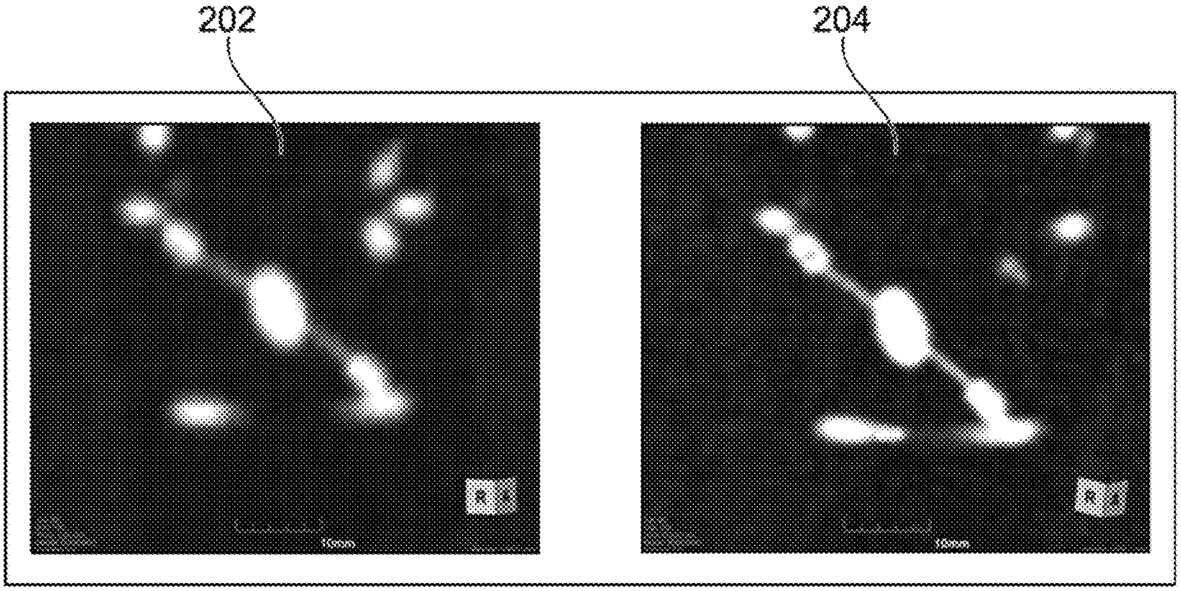
FIG. 2 exemplarily illustrates a screenshot of original 3D full CT scan and targeted CT image acquisition of a 3D printed abnormality, according to an embodiment of the present invention.

FIG. 2 exemplarily illustrates a screenshot of original 3D full scan 202 and targeted image 204 of an abnormality, according to an embodiment of the present invention. The targeted image 202 enables to visualize a small air structure in the frame that holds the 3D printed ellipsoids. However, the air bubble structure is completely missing from the original 3D full scan 202. In addition, the data quality and visualization of the 1.25 mm diameter cylinders intersecting the ellipsoids is far better in the targeted image 204 acquisition.

Figure 3:
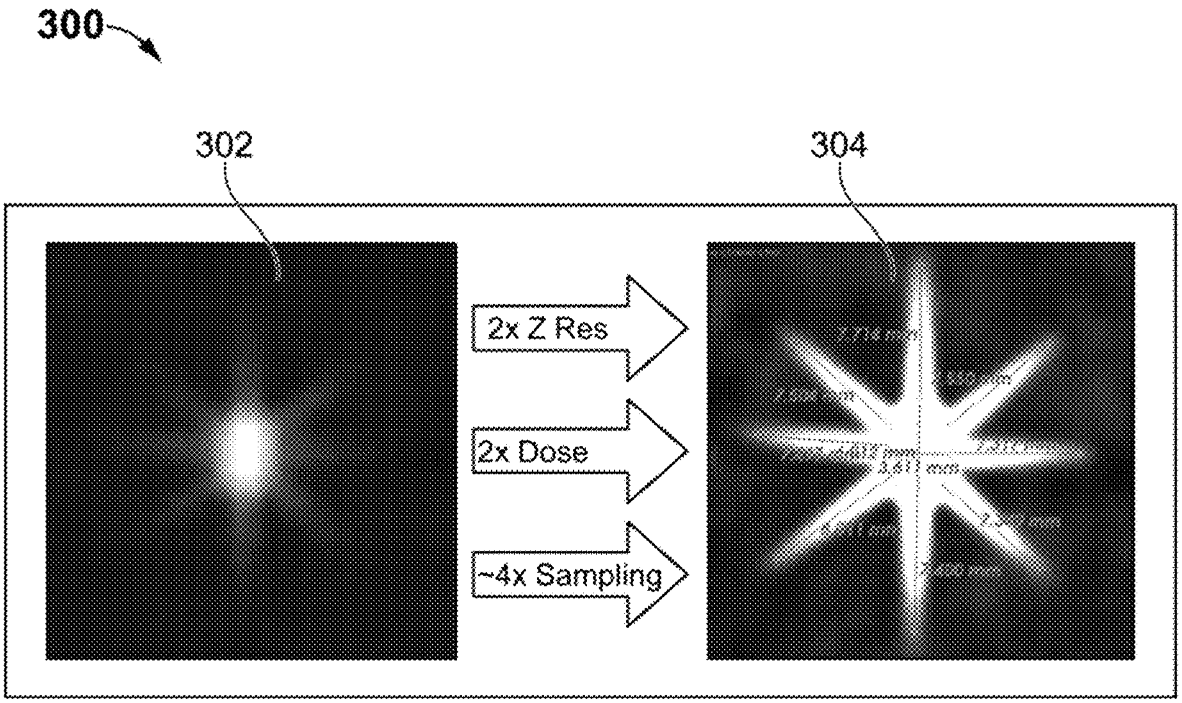
FIG. 3 exemplarily illustrates a screenshot of a typical CT acquisition and targeted image of a 3D printed abnormality, according to an embodiment of the present invention.

FIG. 3 exemplarily illustrates a screenshot 300 of a typical CT acquisition 302 and targeted image 304 of an abnormality, according to an embodiment of the present invention. The typical CT acquisition 302 shows a small ellipsoid object with 8 cones emanating from the object.

If an AI targeting and image optimization system 108 detects this object and determines it has high risk to the patient and an additional high-quality acquisition or reconstructions would be beneficial, the AI targeting and image optimization system 108 could recommend half the slice thickness and spacing, 2 times the dose, and 4 times the image sampling along each of three dimensions. This would result in 64 times the amount of image data collected within the targeted area and result in the image quality shown in the targeted image 304. The targeted image 304 would be of immediate benefit to the radiologist as it contains far more information resulting in the ability to better visualize and measure the abnormality within the targeted region. In addition, a fully optimized measurement system consisting of both high-quality targeted image data acquisition and a deep learning or model-based AI algorithm that could leverage and optimize measurement performance for the improved image quality targeted data, will result in much better image measurement performance.

Figure 4:
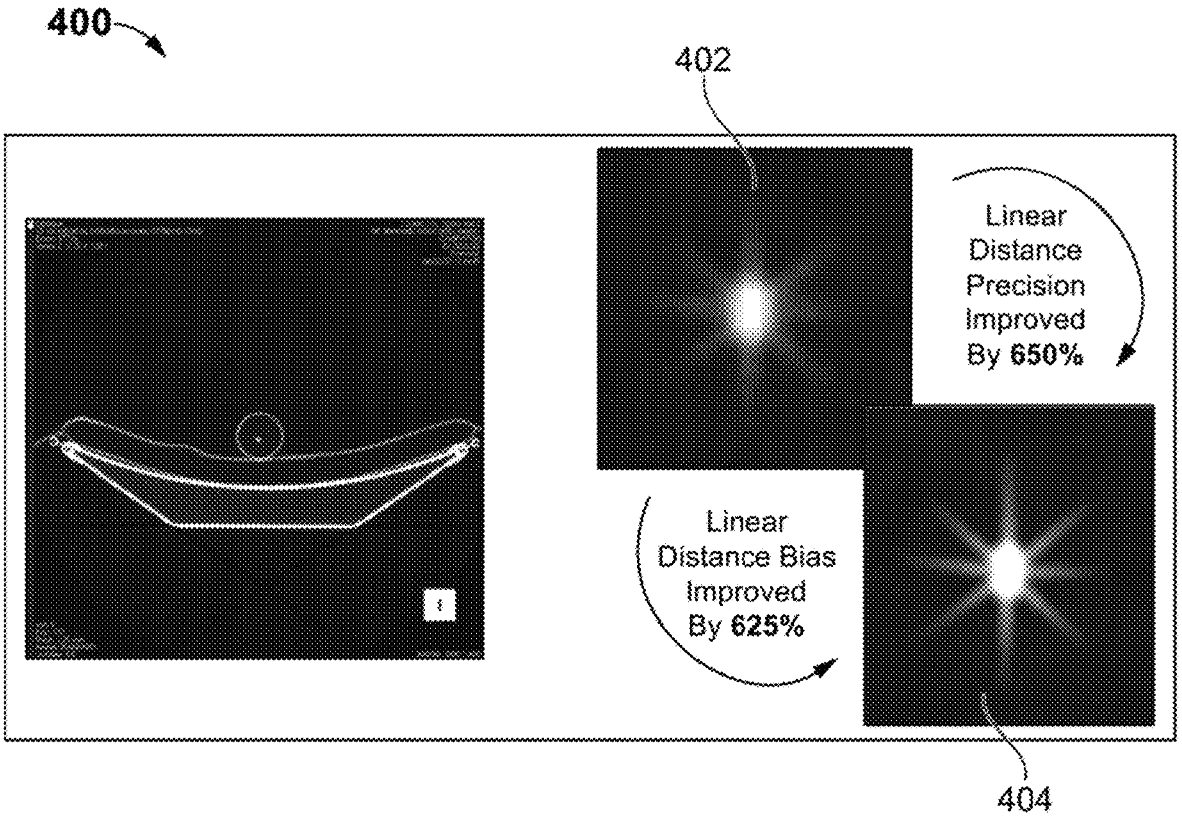
FIG. 4 exemplarily illustrates a screenshot of a typical CT acquisition and targeted image of an abnormality with improved linear distance measurement bias and precision, according to an embodiment of the present invention.

FIG. 4 exemplarily illustrates a screenshot 400 of a typical CT acquisition 402 and targeted image 404 of an abnormality with improved linear distance precision, according to an embodiment of the present invention. In the example shown in FIG. 3 and FIG. 4, the length measurement precision (i.e., coefficient of variation) of the eight cones emanating from the surface of the ellipsoid improved by 650% and the measurement bias (i.e., mean difference from known manufactured length) improved by 625%. Results similar to this have been observed on several different CT scanners from different manufacturers.

The system could aid in the acquisition of better targeted images and to aid the radiologist when reviewing a patient study. This invention allows an AI based detection system identify abnormalities/conditions and a deep learning AI or model-based analysis algorithm to direct a technologist to acquire the best possible data of the abnormalities/conditions so the detection and measurement of the scanner image data and the measurement/analysis algorithm are optimized. The present invention is a fully optimized system, where the image quality properties needed by a quantitative measurement and analysis algorithm are obtained for targeted abnormalities has the potential to produce significantly better quantitative measurement improvements. The image formation simulation engine has the potential to allow for further measurement performance improvements, including the potential to provide meaningful confidence intervals for the resulting quantitative measurements.

The foregoing description comprises illustrative embodiments of the present disclosure. Having thus described exemplary embodiments of the present disclosure, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method.

Many modifications and other embodiments of the disclosure will come to mind to one skilled in the art to which this disclosure pertains having the benefit of the teachings presented in the foregoing descriptions. Although specific terms may be employed herein, they are used only in generic and descriptive sense and not for purposes of limitation. Accordingly, the present disclosure is not limited to the specific embodiments illustrated herein. While the above is a complete description of the preferred embodiments of the disclosure, various alternatives, modifications, and equivalents may be used. Therefore, the above description and the examples should not be taken as limiting the scope of the disclosure, which is defined by the appended claims.

The invention claimed is:

1. A method for obtaining quality image data and measurements from a medical imaging device, comprising the steps of:
   operating a medical scanner to obtain an image of a subject;
   analyzing the image with any combination of model-based and deep learning AI methods to find one or more target areas of abnormalities;
   analyzing one or more target areas of abnormality of the image to determine a set of targeted scan parameters for the medical scanner for visualizing and automatically quantitatively measuring the abnormality,
   providing information including target image acquisition protocol data to a user to perform an additional targeted image acquisition or image reconstruction, and
   providing a radiological image viewer to display both the image and targeted images from targeted image acquisition in a same viewing window using registered image overlays.

2. The method of claim 1, further comprising the step of: calculating automated measurement of the abnormality with the target image acquisition protocol data.

3. The method of claim 1, wherein the medical scanner is at least one of Computed Tomography (CT), Magnetic Resonance (MR), Positron Emission Tomography (PET), X-ray Radiography (XR), and Ultrasound (US) scanner.

4. The method of claim 1, wherein the target image acquisition data includes the set of targeted scan parameters, wherein the targeted scan parameters are determined by any combination of a calibration optimized protocol database, model-based analysis methods, deep learning AI analysis methods, simulation methods, and prior clinical guidance information.

5. The method of claim 1, wherein the target image acquisition data includes a set of targeted scan parameters and automated measurement algorithms, wherein the targeted scan parameters and automated measurement algorithms are determined by any combination of a calibration optimized protocol database, model-based analysis methods, deep learning AI analysis methods, simulation methods, and prior clinical guidance information.

6. The method of claim 5, wherein the automated measurement algorithm uses an image formation simulation engine to estimate automated measurement properties including measurement bias and measurement precision.

7. The method of claim 1, wherein the analysis of the target areas for assessing the severity of the abnormality is performed based on fundamental image quality characteristics of the image to determine the targeted acquisition data.

8. The method of claim 7, wherein the image quality characteristics includes resolution, noise and sampling rate.

9. A system for obtaining quality image data and measurements from a medical imaging device, comprising:
   medical scanner configured to obtain image of a patient, and an artificial intelligence (AI) targeting and image optimization system configured to:
   receive and analyze the image with any combination of model-based and deep learning AI methods to find one or more target areas of abnormalities;
   analyze one or more target areas of abnormality of the image to determine a set of targeted scan parameters for the medical scanner for visualizing and automatically quantitatively measuring the abnormality,
   provide information including a target image acquisition data to a user to perform an additional targeted image acquisition or image reconstruction, and
   enable the user to select one or more target areas of abnormality of the image to determine the targeted scan parameters and provide a radiological image viewer to display both the image and targeted images from targeted image acquisition in a same viewing window using registered image overlays.

10. The system of claim 9, wherein the medical scanner is monitored and optimized using an automated calibration phantom monitoring and optimization system.

11. The system of claim 9, wherein the AI targeting and image optimization system is configured to calculate automated measurement of the abnormality with the target image acquisition data.

12. The system of claim 9, wherein the medical scanner is at least one of Computed Tomography (CT), Magnetic Resonance (MR), Positron Emission Tomography (PET), X-ray Radiography (XR), and Ultrasound (US) scanner.

13. The system of claim 9, wherein the target image acquisition data includes the set of targeted scan parameters, wherein the targeted scan parameters are determined by any combination of a calibration optimized protocol database, model-based analysis methods, deep learning AI analysis methods, simulation methods, and prior clinical guidance information.

14. The system of claim 9, wherein the target image acquisition data includes a set of targeted scan parameters and automated measurement algorithms, wherein the targeted scan parameters and automated measurement algorithms are determined by any combination of a calibration optimized protocol database, model-based analysis methods, deep learning AI analysis methods, simulation methods, and prior clinical guidance information.

15. The system of claim 14, wherein the automated measurement algorithm uses an image formation simulation engine to estimate automated measurement properties including measurement bias and measurement precision.

16. The system of claim 9, wherein the analysis of the target areas for assessing the severity of the abnormality is performed based on fundamental image quality characteristics of the image and determine the targeted acquisition data, wherein the image quality characteristics includes resolution, noise and sampling rate.

17. A method for obtaining quality image data and measurements from a medical imaging device, comprising the steps of:
   operating a medical scanner to obtain an image of a subject;
   analyzing the image with any combination of models and AI methods to find one or more target areas of abnormalities;
   analyzing one or more target areas of abnormality of the image to determine a set of targeted scan parameters for the medical scanner for visualizing and automatically quantitatively measuring the abnormality;
   providing information including target image acquisition data to a user to perform an additional targeted image acquisition or image reconstruction, wherein the target image acquisition data includes the set of targeted scan parameters, and calculating automated measurement of the abnormality using the target image acquisition data, and
   enabling the user to select one or more target areas of abnormality of the image to determine the targeted scan parameters and providing a radiological image viewer to display both the image and targeted images from targeted image acquisition in a same viewing window using registered image overlays.

* * * * *